US006575161B1

(12) United States Patent
Nilsson

(10) Patent No.: US 6,575,161 B1
(45) Date of Patent: Jun. 10, 2003

(54) POWDER CLASSIFICATION DEVICE

(75) Inventor: Lars-Gunnar Nilsson, Köping (SE)

(73) Assignee: Microdrug AG, Hergeswil (CH)

( * ) Notice: Subject to any disclaimer, the term of this patent is extended or adjusted under 35 U.S.C. 154(b) by 0 days.

(21) Appl. No.: 09/744,740

(22) PCT Filed: Jul. 8, 1999

(86) PCT No.: PCT/SE99/01242

§ 371 (c)(1),
(2), (4) Date: Jan. 29, 2001

(87) PCT Pub. No.: WO00/06235

PCT Pub. Date: Feb. 10, 2000

(30) Foreign Application Priority Data

Jul. 30, 1998 (SE) .............................................. 9802649

(51) Int. Cl.$^7$ .............................................. A61M 15/00
(52) U.S. Cl. .............................. 128/203.15; 128/203.12
(58) Field of Search ....................... 128/200.11, 200.12, 128/200.14, 200.16–200.18, 200.21–200.24, 203.15, 203.12, 203.19, 202.25; 239/3, 690, 690.1, 695, 696, 699, 700, 708, 102.2

(56) References Cited

U.S. PATENT DOCUMENTS

| | | | | |
|---|---|---|---|---|
| 4,772,982 A | * 9/1988 | Nagasaka | 361/227 |
| 5,115,971 A | * 5/1992 | Greenspan et al. | 239/3 |
| 5,577,497 A | * 11/1996 | Mecikalski et al. | 128/203.15 |
| 5,669,973 A | * 9/1997 | Pletcher | 118/624 |
| 5,694,920 A | * 12/1997 | Abrams et al. | 128/200.16 |
| 5,823,434 A | * 10/1998 | Cooper | 128/200.16 |
| 5,857,456 A | * 1/1999 | Sun et al. | 128/203.12 |
| 5,871,010 A | * 2/1999 | Datta et al. | 128/203.12 |
| 5,894,841 A | * 4/1999 | Voges | 128/200.14 |
| 5,938,118 A | * 8/1999 | Cooper | 128/200.16 |
| 6,007,630 A | * 12/1999 | Pletcher et al. | 118/624 |
| 6,012,454 A | * 1/2000 | Hodson et al. | 128/203.15 |
| 6,026,809 A | * 2/2000 | Abrams et al. | 128/200.22 |
| 6,089,227 A | * 7/2000 | Nilsson | 128/203.12 |
| 6,105,877 A | * 8/2000 | Coffee | 128/204.21 |
| 6,142,146 A | * 11/2000 | Abrams et al. | 128/203.15 |
| 6,152,130 A | * 11/2000 | Abrams et al. | 128/203.12 |
| 6,196,218 B1 | * 3/2001 | Voges | 128/200.14 |
| 6,202,945 B1 | * 3/2001 | Yasuda et al. | 239/704 |
| 6,237,590 B1 | * 5/2001 | Leedom et al. | 128/203.12 |
| 6,237,591 B1 | * 5/2001 | Jackson | 128/203.12 |
| 6,298,847 B1 | * 10/2001 | Datta et al. | 128/203.12 |
| 6,308,704 B1 | * 10/2001 | Wennerberg | 128/203.12 |
| 6,394,086 B1 | * 5/2002 | Barnes et al. | 128/203.15 |
| 6,397,840 B1 | * 6/2002 | Chrai et al. | 128/202.25 |
| 6,457,470 B1 | * 10/2002 | Coffee | 128/200.14 |

FOREIGN PATENT DOCUMENTS

JP 53074971 * 7/1978 .................... 239/3

* cited by examiner

*Primary Examiner*—Weilun Lo
*Assistant Examiner*—Teena Mitchell
(74) *Attorney, Agent, or Firm*—Young & Thompson

(57) ABSTRACT

The invention discloses a method and a device for classification and, if required, electrostatic charging of a resulting separated decomposed powder preferably in the form of a substance intended for inhalation purposes. The classification takes place in that the powder is released from a device decomposing the suitable substance, whereby the powder is given a velocity perpendicular to in applied electric field (8). By adapting the strength of the electric field decomposed powder, i.e. individual particles resembling dust, will by means of the electric field (8) be attracted to a device (9) from which dosing of the individual particles then takes place. Larger particles (agglomerates) then will proceed straight ahead in an initial velocity direction as their kinetic energy is essentially larger than that for the small particles. In this manner a desirable separation of individual particles is obtained from the heavier agglomerated particles not desired to be administered and the conditions for a very good dosing of the substance thereby will result.

9 Claims, 3 Drawing Sheets

```
┌─────────────────┐
│ Powder is carried│  20
│   to magazine    │
└────────┬────────┘
         ▼
┌─────────────────┐
│ Powder is carried│  22
│to releasing device│◄──────┐
└────────┬────────┘         │
         ▼                  │
┌─────────────────┐         │
│   Releasing of   │  24    │
│ decomposed powder│        │
└────────┬────────┘         │
         ▼                  │
┌─────────────────┐   ┌─────┴──────────┐
│  Classification  │26 │ Means for bringing│ 28
│                 │──▶│   powder back    │
└────────┬────────┘   └─────▲──────────┘
         ▼                  │
┌─────────────────┐         │
│   Compartment    │  30    │
│    for dust      │        │
└────────┬────────┘         │
         ▼                  │
┌─────────────────┐         │
│ Decomposed powder│──32────┘
│  to dosing device│
└────────┬────────┘
         ▼
┌─────────────────┐
│    Regulation    │  34
└────────┬────────┘
         ▼
┌─────────────────┐        ┌──────────────┐
│  Mixing with air │──36──▶│ Administering│ 38
└─────────────────┘        └──────────────┘
```

Figure 1

POWDER CLASSIFICATION DEVICE

TECHNICAL FIELD

The present invention relates to a device for de-agglomeration and electrostatic charging of a pulverized powder for inhalation by means of stationary or portable devices, whereby powder refers to active pharmaceutical substances and mixtures and specially treated preparations intended to be administered via the respiratory tract.

BACKGROUND AND PRIOR ART

Administering of medical powders today is performed in numerous ways. Within health care more and more is focussed on the possibility of dosing powder directly to the lungs by means of an inhaler to obtain an effective, quick and patient-friendly administering.

For the medical powders, being administered by means of an inhaler, to land in the lungs, the powder should have a grain size of 1 to 6 $\mu$m. A larger grain size will stick in the mouth and throat and a smaller grain size accompanies the expiration air.

Powder having a small grain size will have a strong tendency of agglomerating, i.e. to get conglomerated. In the inhalers. which are used today, a large extent of the active substance is in the form of agglomerates when it is dosed and much powder therefore will stick in the upper respiratory tract. Different ways to de-agglomerate the powder have been developed and in most cases the inhalation air is utilized for decomposing the agglomerates.

It is also common to use carriers having a larger grain size onto which the fine powder is distributed. Upon inspiration the large grains will then stick in the oral cavity while the small grains are set free and proceed to the lungs. Certain manufacturers also use electrically driven propellers, piezo-vibrators and/or mechanical vibration to decompose the agglomerates. Thus, achieving a very large portion of individual particles in the inspiratory air is a very important factor for obtaining a high degree of effectiveness upon inhalation.

As a complete de-agglomeration is difficult to achieve it is desirable that an additional separation stage is inserted in the form of a classification, which separates remaining agglomerates from the decomposed individual particles.

In the Swedish patent publication SE 504 458 a device for an inhaler is disclosed, which utilizes a rotating drum as dosing device together with an electric field, which document hereby is incorporated by reference.

DESCRIPTION OF THE INVENTION

The present invention discloses a method and a device for classification and, if required, electrostatic charging of a resulting fine powder especially intended for inhalation purposes. The electrostatic charging takes place by means of tribo-, corona- and/or induction-charging. Charging of the powder is from now on referring to an electrostatic charging according to any of the mentioned ways or a combination of those. Particularly the present invention is intended for use in dosing powder directly to the inspiratory air, alternatively providing a dosing device with electrostatically charged de-agglomerated powder for a more controlled dosing to the inspiratory air, alternatively application to a carrier for further preparation and introduction to an inhaler or other device, e.g., a piece of plaster or the like.

The classification preferably takes place in that the electrostatically charged powder is separated by a device decomposing a suitable substance, whereby the powder is given appropriate velocity. The powder is in this manner conveyed into an electric field, which preferably is perpendicular to the direction of the powder motion. By adapting the strength of the electric field decomposed powder, i.e. individual particles resembling dust, will by the electric field be attracted to a device from which dosing of individual particles takes place. The larger particles (the agglomerates) will proceed straight ahead in an original direction of motion as their kinetic energy is essentially larger than that for the small particles. In this manner an almost complete separation of individual particles from heavier agglomerated particles is obtained and a prerequisite for a very good dosing of the substance thereby will exist.

The device for accelerating the powder to an appropriate velocity is designed, according to different embodiments of the present invention, as a rotating brush flipping the powder, a vibrating membrane, a piezo-electric member or a fan. It is important to achieve an even and controllable acceleration of the powder, as the velocity should be adapted to the electric field and the distance to the reception device.

At the same time as the powder is accelerated, the powder preferably is electrostatically charged by selection of appropriate techniques and material. To obtain correct potential and correct sign of the potential an appropriate material must be selected and this takes place by considering how different materials are positioned in the tribo-electric series. The distance between two materials where tribo-charging takes place give rise to a possibility to control the potential strength intended to be achieved.

The process takes place in a classification device where releasing from a de-agglomeration zone takes place in a direction towards a reception device and where an electric field is arranged perpendicular to the direction of release. The kinetic energy, which is essentially larger for the heavier agglomerates, then swill carry the large particles to the reception device, while the small individual dust resembling particles will be made to attract a dosing drum by means of the electric field. In this way only the individual particles in practice will be utilized for dosing. A thin layer of electrostatically charged particles will thereby place themselves onto the rotatory dosing drum.

The dosing then takes place, for instance, by means of an attracting electrode having an appropriate voltage attracting the small powder grains from the dosing drum. An airstream, the inspiratory air, will carry away the powder grains before they reach the attracting electrode. The amount of dosed powder can be governed by connecting and disconnecting the voltage. Alternatively, the dosing may be regulated by inserting an electronic filter between the dosing drum and the attracting electrode. A further alternative for governing the dosing is to vary the electric field in the classification device.

The invention is defined by the independent claims 1 and 3 and different embodiments are defined by the dependent claims 2–4 and 6–9.

BRIEF DESCRIPTION OF THE DRAWINGS

The invention will be described in the form of a preferred illustrative embodiment and by, means of the attached drawings wherein like reference numbers indicate like or corresponding elements and wherein:

FIG. 1 illustrates a principal sketch of the path of powder through an administering device comprising the classification device according to the present invention;

DESCRIPTION OF AN ILLUSTRATIVE EMBODIMENT

Figure 2:
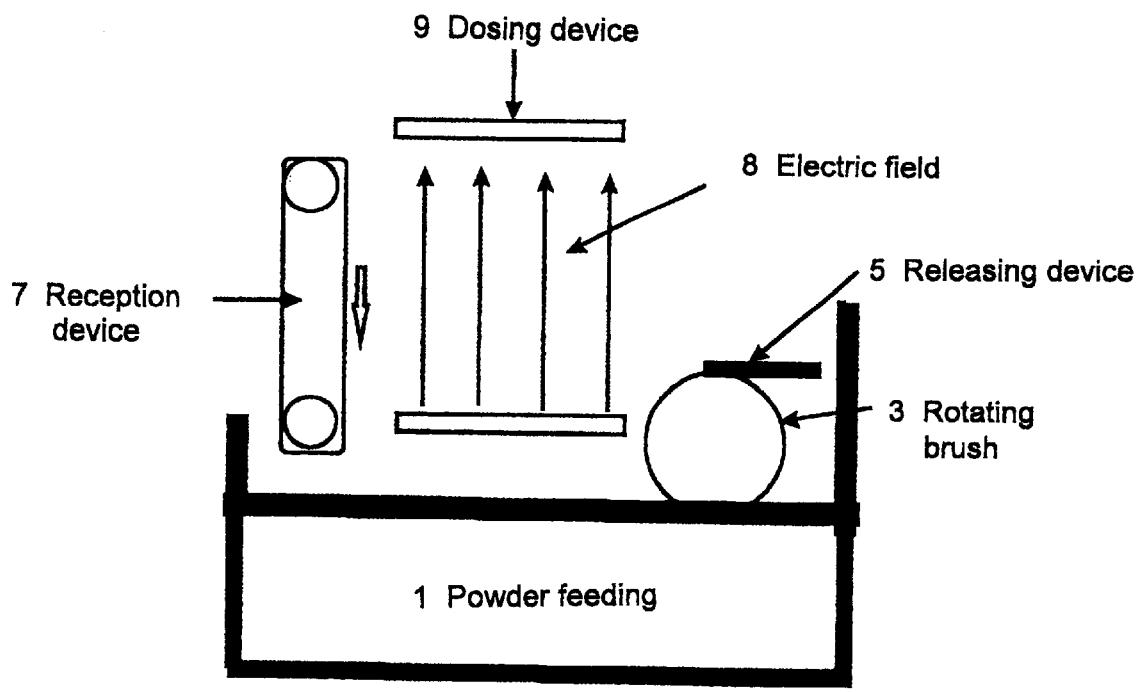
FIG. 2 illustrates a principal sketch of the classification device in an illustrative embodiment which can be used with the method according to FIG. 1.
Figure 3:
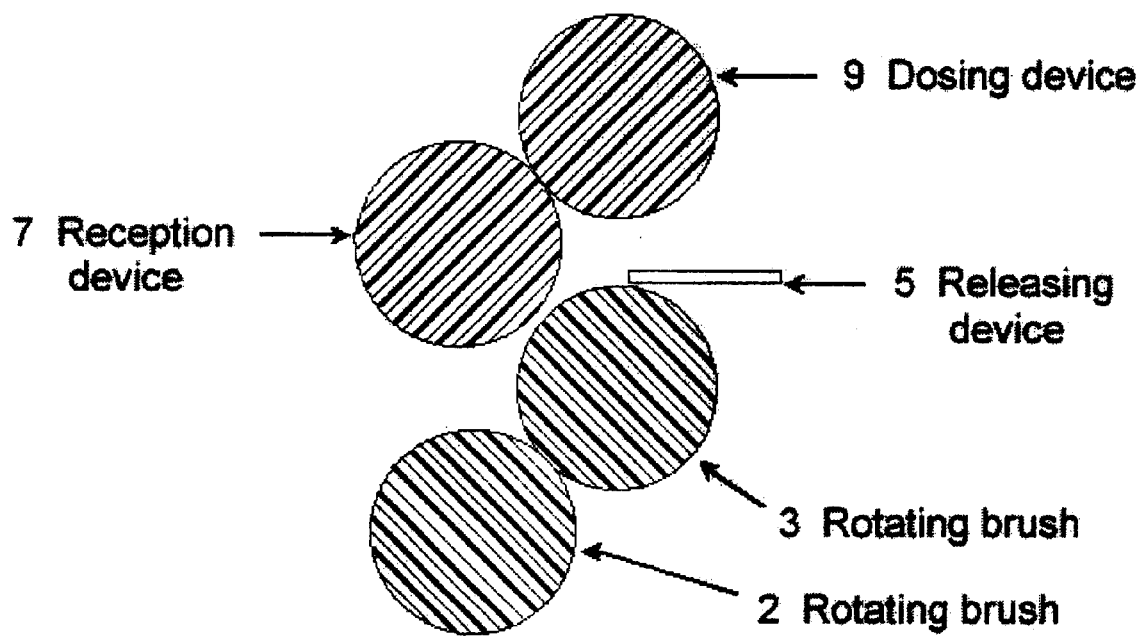
FIG. 3 illustrates more in detail an embodiment for preparing the powder according to FIG. 1 with simultaneous classification.

Substances intended at first hand to be prepared are medical powders, but also other powders where an exact dosing of small quantities is needed may be considered. From now on in connection with the description of an illustrative embodiment powder will be used as a common word for all types of substances or preparations of substances, which shall be treated for utilization in an inhaler.

FIG. 1 describes the method according to the present invention in a schematic way by means of a flow chart illustrating the path of the powder through the classification device. The powder feeding comprises a pretreatment and a magazine where also superfluous powder may be brought back. The design of this unit is beyond the scope of the present application and is therefore not further described in this context.

According to the flow chart presented in FIG. 1 powder is first, in a step 20, carried to a magazine from where it then, in a step 22, is carried to a decomposition means. In a step 24, the decomposed powder and remaining agglomerates will be released from the decomposition device to a classification step 26. The classification step 26 separates the small decomposed particles from the remaining agglomerates, which are carried back to a reception means in a bring back step 28. By means of the classification step 26. particle dust is created in the step 30. The particle dust of step 30 is carried through the applied electric field to a dosing device. From the dosing device powder is carried via a regulation step 34 further for mixing with air in a step 36 and finally for administering in a step 38. From the dosing device superfluous particles are carried back to the reception means in a step 32. Thereby in the bringing back step 26 also superfluous decomposed small particles together with remaining agglomerates are carried back to the decomposition means or to the magazine.

In FIG. 2 in a principal sketch is demonstrated a device for classification of powder according to the method of the present invention. A releasing device 5 releases powder from a device 1 feeding powder. The releasing device in an illustrative embodiment consists of a plate of metal or plastic, which presses against a rotating brush filled with powder, such that its bristles are slightly bent. When the bristles of the brush have passed the releasing device 5 the bristles of the brush are straightened, whereby the powder particles will be flipped or launched in the tangential direction of the brush and in the direction towards a reception device 7. Between the brush for feeding of powder and the reception device there is an electric field 8 positioned perpendicular to the direction of particles obtained. The electric field is preferably static, but may also in a further embodiment be pulsing or adapted to control the dosing. In the direction of the field there is further a dosing device 9, which will catch the particles, which are caught and carried by the electric field in the direction towards the dosing device 9. Heavier, not decomposed agglomerates will be able to pass the electric field and reach the reception device 7, while light individual particles, in the form of fine dust will by the field be separated and carried to the dosing device. To optimize the classification process it may be advantageous to supply both the reception device as well as the dosing drum with an attracting potential, and balance the potentials such that the desirable result is obtained. Depending on the design and desired dosing the potentials, which are required to get the correct field strength, do vary relatively much, but normally these potentials are between 50 and 700 V. In a further embodiment of the device according to the invention a measuring member is applied to the dosing device 9 to regulate and measure charging quality and amount of charging. Such a measuring member can be designed according to the state of the art by the professional.

In FIG. 3 a more detailed device for transport of powder in connection to classification is disclosed. Powder is fed via two rotating brushes 2 and 3 (de-agglomeration device) to a releasing device 5, from which the powder is made to be flipped or to be launched into an electric field (not shown) directed between one of the rotating brushes and a rotating dosing device 9 in the form of a drum. The particles are given a direction of motion towards a reception device 7 in the form of an additional rotating brush. This brush in the present embodiment slightly touches the drum of dosing device 9 to upon its rotation pick up remaining particles on the drum after the dosing. Agglomerates caught by the reception device 7 and from the dosing remaining small particles are brought back to the feeding device 1 (shown in FIG. 2) or to a magazine by means of additional members in the form, for instance, of a further rotating brush (not shown) in engagement with the reception device 7. Thus, the releasing device in the basic embodiment also comprises a rotating brush, the bristles of which are slightly bent backwards by means of a bearing on an edge such that the powder flips off when the bristles are straightened after passing the edge. The plate edge and the brush are made of an appropriate material, which then is adapted to the characteristics of the powder and whether an electrostatic charging of the powder is desired. It is also considered which potential is desired for the powder. The materials selected shall have an appropriate conductivity, which is also adapted to the characteristics of powder and other materials incorporated. A conductive material is selected if it is desirable to avoid that the powder is electrostatically charged. Other manners to design the releasing device are blowing the powder out into the electric field by means of a fan or using a piezo-vibrator or a vibrating membrane. Due to the selection of materials and the design it is possible to govern where and how the electrostatic charging will take place, as well as the potential and sign of the charging.

Thus, the applied electric field 8 is directed perpendicular in relation to the releasing device. The strength of the voltage field is varied dependent on the characteristics of the powder and may then be both static and pulsing. The released grains of powder get a kinetic energy in their direction of motion, large for the large particles and small for the smaller decomposed particles. If the particles are electrostatically charged, they will more easily be influenced by the electric field. which has such a direction that the particles are attracted towards the dosing device. This means that the electric potentials for powder and dosing device have different signs. What will happen during these conditions is that the large particles (the agglomerates) having a high kinetic energy will mainly advance straight ahead and be received by the reception device 7 to be primarily brought back to the decomposition device, i.e. the de-agglomeration zone, while the small decomposed dust resembling particles easily are attracted to the dosing device 9 due to their lower kinetic energy and a higher specific charge. In this manner an effective separation of individual particles and agglomerates is obtained. Appropriate selected distances and potentials of course play an important role in the classification method according to the present invention. An even better classification may in certain cases be obtained by giving the reception device 7 a balanced potential in relation to the dosing device 9.

The agglomerates, which hereby are taken care of by the reception device 7, consequently may simply, as already mentioned, by means of that device be brought back to the powder feeding device 1 or to the magazine.

The material of the apparatus is selected such that the lowest possible amount of deposits is obtained. This takes place by giving the walls a potential repelling the particles, which means that the potential of the walls has the same sign as the charging of the particles.

The method and the device has been disclosed by means of an illustrative embodiment, which should however not be taken as limiting the scope of the invention, which is defined by the attached claims.

What is claimed is:

1. A method of separating electrostatically charged individual powder particles from agglomerated powder particles that are in a mixture of the individual and agglomerated powder particles, the method comprising the steps of:
   placing the mixture on a releasing device;
   creating an electric field that extends in a first direction toward a dosing device that is to receive the individual powder particles, the electric field being between the releasing device and a reception device that is to receive the agglomerated powder particles; and
   impelling the mixture from the releasing device into the electric field in a second direction generally perpendicular to the first direction, wherein kinetic energy of the agglomerated powder particles carries the agglomerated powder particles through the electric field to the reception device and the electric field carries the individual powder particles to the dosing device.

2. The method of claim 1, wherein the placing step comprises the step of carrying the mixture on bristles of a brush and the impelling step comprises the steps of bending and releasing the bristles to flip the mixture from the bristles in the second direction.

3. The method of claim 2, wherein the brush is rotating and the bristles rotate through a container for the mixture before encountering a plate that bends and releases the bristles.

4. The method of claim 1, further comprising the steps of removing the agglomerated powder particles from the reception device, returning the removed particles to the releasing device, and repeating the impelling step.

5. A device for separating individual powder particles from agglomerated powder particles that are in a mixture of the individual and agglomerated powder particles, comprising:
   a releasing device that receives the mixture;
   a dosing device that receives the individual powder particles;
   a reception device that receives the agglomerated powder particles;
   an electric field that extends in a first direction toward said dosing device, the electric field being between said releasing device and said reception device; and
   an impelling apparatus that impels the mixture from said releasing device into the electric field in a second direction generally perpendicular to the first direction, wherein kinetic energy of the agglomerated powder particles carries the agglomerated powder particles through the electric field to said reception device and the electric field carries the individual powder particles to said dosing device.

6. The device of claim 5, wherein said releasing device comprises a rotating brush with bristles,
   wherein said impelling apparatus comprises a plate adjacent to said rotating brush so that said plate bends and releases said bristles as said rotating brush rotates to flip the mixture in the second direction, and
   further comprising a container for the mixture, said bristles entering said container to receive the mixture as said rotating brush rotates.

7. The device of claim 6, wherein said reception device is arranged to place the agglomerated powder particles received thereon in said container.

8. The device of claim 5, wherein said reception device comprises a conveyor.

9. The device of claim 5, wherein said dosing device and said reception device each comprises a rotating brush.

* * * * *